United States Patent
Chao et al.

(10) Patent No.: US 11,471,457 B2
(45) Date of Patent: Oct. 18, 2022

(54) METHOD OF TREATING EPITHELIAL GROWTH FACTOR RECEPTOR (EGFR) T790M-POSITIVE NON-SMALL CELL LUNG CANCER BY ADMINISTERING A COMBINATION OF A VEGFR-2 ANTIBODY AND OSIMERTINIB

(71) Applicants: Eli Lilly and Company, Indianapolis, IN (US); Medimmune Limited, Granta Park (GB)

(72) Inventors: Bo Hua Chao, Summit, NJ (US); Sang Min Lee, Weehawken, NJ (US)

(73) Assignees: Eli Lilly and Company, Indianapolis, IN (US); Medimmune Limited, Granta Park Cambidge (GB)

( * ) Notice: Subject to any disclaimer, the term of this patent is extended or adjusted under 35 U.S.C. 154(b) by 0 days.

(21) Appl. No.: 16/633,230

(22) PCT Filed: Aug. 20, 2018

(86) PCT No.: PCT/US2018/047031
§ 371 (c)(1),
(2) Date: Jan. 23, 2020

(87) PCT Pub. No.: WO2019/040348
PCT Pub. Date: Feb. 28, 2019

(65) Prior Publication Data
US 2020/0155551 A1      May 21, 2020

Related U.S. Application Data

(60) Provisional application No. 62/672,153, filed on May 16, 2018, provisional application No. 62/664,529, filed on Apr. 30, 2018, provisional application No. 62/548,069, filed on Aug. 21, 2017.

(51) Int. Cl.
*A61K 31/506* (2006.01)
*A61P 35/00* (2006.01)
*A61K 9/00* (2006.01)
*A61K 39/395* (2006.01)

(52) U.S. Cl.
CPC .......... *A61K 31/506* (2013.01); *A61K 9/0053* (2013.01); *A61K 39/3955* (2013.01); *A61P 35/00* (2018.01)

(58) Field of Classification Search
CPC ................ A61K 31/506; A61K 9/0053; A61K 39/3955; A61K 2039/505; A61P 35/00; C07K 16/2863
See application file for complete search history.

(56) References Cited

FOREIGN PATENT DOCUMENTS

WO      2015/134242      9/2015

OTHER PUBLICATIONS

ClinicalTrials.gov (Jun. 3, 2016). Identifier No. NCT02789345—"A Study of Ramucirumab (LY3009806) or Necitumumab (LY3012211) Plus Osimertinib in Participants With Lung Cancer".*
International Search Report for PCT/US2018/047031.
Written Opinion for PCT/US2018/047031.
Sullivan, et al., "Osimertinib in the treatment of patients with epidermal growth factor receptor T790M mutation-positive metastatic non-small cell lung cancer: clinical trial evidence and experience," Therapeutic Advances in Respiratory Disease, col. 10(6), pp. 549-565 (2016).
Planchard, et al., "Phase 1 Study of Ramucirumab or Necitumumab in Combination with Osimertinib (AZD9291) in Advanced T790M-Positive EGFR-Mutant NSCLC," https://www.jto.org/article/S1556-0864(16)32739-3/pdf, Jan. 2017; XP002786877.
Cobo, et al., "Spotlight on ramucirumab in the treatment of nonsmall cell lung cancer: design, development, and clinical activity," Lung Cancer: Targets and Therapy, vol. 8, pp. 57-66 (2017).
Akamatsu, et al., "Osimertinib With Ramucirumab in EGFR-mutated, T790M-positive Patients with Progression During EGFR-TKI Therapy: Phase Ib Study," Clinical Lung Cancer Nov. 1, 2018 Elsevier Inc. USA, vol. 19, No. 6, pp. E871-e874 (2018).
Yu, et al., "Osimertinib with ramucirumab or necitumamab in advanced T790M-positive EGFR-mutant NSCLC: Preliminary PH1 study results," Journal of Thoracid Oncology Nov. 1, 2017 Elsevier Inc. NLD, Vold 12, No. 11, Supplement 2, pp. S1972 CONF Oct. 15, 2017 to Oct. 18, 2017 (2017).
Paz-Ares, "CNS Activity of Ramucirumab in Combination with Osimertinib in Patients with Advanced T790M-Positive EGFR-Mutant NSCLC," Journal of Thoracic Oncology, IASLC 19th World Conference on Lung Cancer Oct. 1, 2018 Elsevier Inc. NLD, vol. 13, No. 10, Supplement, pp. S453 Sep. 23, 2018 to Sep. 26, 2018 (2018).

* cited by examiner

*Primary Examiner* — Robert S Landsman
(74) *Attorney, Agent, or Firm* — Grant Reed

(57) ABSTRACT

The present invention relates to a combination of anti-human VEGFR-2 antibodies and human EGFR tyrosine kinase inhibitors for the treatment of T790M-positive EGFR-mutant non-small cell lung cancer.

12 Claims, No Drawings
Specification includes a Sequence Listing.

SEQUENCE LISTING

<160> NUMBER OF SEQ ID NOS: 5

<210> SEQ ID NO 1
<211> LENGTH: 107
<212> TYPE: PRT
<213> ORGANISM: Artificial sequence
<220> FEATURE:
<223> OTHER INFORMATION: Synthetic Construct

<400> SEQUENCE: 1

Asp Ile Gln Met Thr Gln Ser Pro Ser Ser Val Ser Ala Ser Ile Gly
1               5                   10                  15

Asp Arg Val Thr Ile Thr Cys Arg Ala Ser Gln Gly Ile Asp Asn Trp
            20                  25                  30

Leu Gly Trp Tyr Gln Gln Lys Pro Gly Lys Ala Pro Lys Leu Leu Ile
         35                  40                  45

Tyr Asp Ala Ser Asn Leu Asp Thr Gly Val Pro Ser Arg Phe Ser Gly
     50                  55                  60

Ser Gly Ser Gly Thr Tyr Phe Thr Leu Thr Ile Ser Ser Leu Gln Ala
 65                  70                  75                  80

Glu Asp Phe Ala Val Tyr Phe Cys Gln Gln Ala Lys Ala Phe Pro Pro
                 85                  90                  95

Thr Phe Gly Gly Gly Thr Lys Val Asp Ile Lys
             100                 105

<210> SEQ ID NO 2
<211> LENGTH: 116
<212> TYPE: PRT
<213> ORGANISM: Artificial sequence
<220> FEATURE:
<223> OTHER INFORMATION: Synthetic Construct

<400> SEQUENCE: 2

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
             20                  25                  30

Ser Met Asn Trp Val Arg Gln Ala Pro Gly Lys Gly Leu Glu Trp Val
         35                  40                  45

Ser Ser Ile Ser Ser Ser Ser Tyr Ile Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Val Thr Asp Ala Phe Asp Ile Trp Gly Gln Gly Thr Met Val
             100                 105                 110

Thr Val Ser Ser
         115

<210> SEQ ID NO 3
<211> LENGTH: 214
<212> TYPE: PRT
<213> ORGANISM: Artificial sequence
<220> FEATURE:
<223> OTHER INFORMATION: Synthetic Construct

<400> SEQUENCE: 3

Asp Ile Gln Met Thr Gln Ser Pro Ser Ser Val Ser Ala Ser Ile Gly
1               5                   10                  15

Asp Arg Val Thr Ile Thr Cys Arg Ala Ser Gln Gly Ile Asp Asn Trp
             20                  25                  30

Leu Gly Trp Tyr Gln Gln Lys Pro Gly Lys Ala Pro Lys Leu Leu Ile
         35                  40                  45

Tyr Asp Ala Ser Asn Leu Asp Thr Gly Val Pro Ser Arg Phe Ser Gly
     50                  55                  60

Ser Gly Ser Gly Thr Tyr Phe Thr Leu Thr Ile Ser Ser Leu Gln Ala
 65                  70                  75                  80

Glu Asp Phe Ala Val Tyr Phe Cys Gln Gln Ala Lys Ala Phe Pro Pro
                 85                  90                  95

Thr Phe Gly Gly Gly Thr Lys Val Asp Ile Lys Arg Thr Val Ala Ala

```
            100                 105                 110
Pro Ser Val Phe Ile Phe Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 4
<211> LENGTH: 446
<212> TYPE: PRT
<213> ORGANISM: Artificial sequence
<220> FEATURE:
<223> OTHER INFORMATION: Synthetic Construct

<400> SEQUENCE: 4

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Thr Asp Ala Phe Asp Ile Trp Gly Gln Gly Thr Met Val
            100                 105                 110

Thr Val Ser Ser Ala Ser Thr Lys Gly Pro Ser Val Leu Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
```

-continued

```
                        245                 250                 255
Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 5
<211> LENGTH: 1356
<212> TYPE: PRT
<213> ORGANISM: Homo sapiens

<400> SEQUENCE: 5

Met Gln Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
                20                  25                  30

Arg Leu Ser Ile Gln Lys Asp Ile Leu Thr Ile Lys Ala Asn Thr Thr
            35                  40                  45

Leu Gln Ile Thr Cys Arg Gly Gln Arg Asp Leu Asp Trp Leu Trp Pro
        50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
                100                 105                 110

Val Ile Tyr Val Tyr Val Gln Asp Tyr Arg Ser Pro Phe Ile Ala Ser
            115                 120                 125

Val Ser Asp Gln His Gly Val Val Tyr Ile Thr Glu Asn Lys Asn Lys
        130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175
```

```
Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Gly Tyr Arg Ile Tyr
    210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
            260                 265                 270

Val Asn Arg Asp Leu Lys Thr Gln Ser Gly Ser Glu Met Lys Lys Phe
        275                 280                 285

Leu Ser Thr Leu Thr Ile Asp Gly Val Thr Arg Ser Asp Gln Gly Leu
        290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
            325                 330                 335

Glu Ser Leu Val Glu Ala Thr Val Gly Glu Arg Val Arg Ile Pro Ala
        340                 345                 350

Lys Tyr Leu Gly Tyr Pro Pro Pro Glu Ile Lys Trp Tyr Lys Asn Gly
        355                 360                 365

Ile Pro Leu Glu Ser Asn His Thr Ile Lys Ala Gly His Val Leu Thr
        370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
            405                 410                 415

Val Tyr Val Pro Pro Gln Ile Gly Glu Lys Ser Leu Ile Ser Pro Val
        420                 425                 430

Asp Ser Tyr Gln Tyr Gly Thr Thr Gln Thr Leu Thr Cys Thr Val Tyr
        435                 440                 445

Ala Ile Pro Pro Pro His His Ile His Trp Tyr Trp Gln Leu Glu Glu
        450                 455                 460

Glu Cys Ala Asn Glu Pro Ser Gln Ala Val Ser Val Thr Asn Pro Tyr
465                 470                 475                 480

Pro Cys Glu Glu Trp Arg Ser Val Glu Asp Phe Gln Gly Gly Asn Lys
            485                 490                 495

Ile Glu Val Asn Lys Asn Gln Phe Ala Leu Ile Glu Gly Lys Asn Lys
        500                 505                 510

Thr Val Ser Thr Leu Val Ile Gln Ala Ala Asn Val Ser Ala Leu Tyr
        515                 520                 525

Lys Cys Glu Ala Val Asn Lys Val Gly Arg Gly Glu Arg Val Ile Ser
530                 535                 540

Phe His Val Thr Arg Gly Pro Glu Ile Thr Leu Gln Pro Asp Met Gln
545                 550                 555                 560

Pro Thr Glu Gln Glu Ser Val Ser Leu Trp Cys Thr Ala Asp Arg Ser
            565                 570                 575

Thr Phe Glu Asn Leu Thr Trp Tyr Lys Leu Gly Pro Gln Pro Leu Pro
        580                 585                 590

Ile His Val Gly Glu Leu Pro Thr Pro Val Cys Lys Asn Leu Asp Thr
```

```
                595                 600                 605
Leu Trp Lys Leu Asn Ala Thr Met Phe Ser Asn Ser Thr Asn Asp Ile
610                 615                 620
Leu Ile Met Glu Leu Lys Asn Ala Ser Leu Gln Asp Gln Gly Asp Tyr
625                 630                 635                 640
Val Cys Leu Ala Gln Asp Arg Lys Thr Lys Arg His Cys Val Val
                    645                 650                 655
Arg Gln Leu Thr Val Leu Glu Arg Val Ala Pro Thr Ile Thr Gly Asn
                660                 665                 670
Leu Glu Asn Gln Thr Thr Ser Ile Gly Glu Ser Ile Glu Val Ser Cys
            675                 680                 685
Thr Ala Ser Gly Asn Pro Pro Pro Gln Ile Met Trp Phe Lys Asp Asn
690                 695                 700
Glu Thr Leu Val Glu Asp Ser Gly Ile Val Leu Lys Asp Gly Asn Arg
705                 710                 715                 720
Asn Leu Thr Ile Arg Arg Val Arg Lys Glu Asp Glu Gly Leu Tyr Thr
                725                 730                 735
Cys Gln Ala Cys Ser Val Leu Gly Cys Ala Lys Val Glu Ala Phe Phe
                740                 745                 750
Ile Ile Glu Gly Ala Gln Glu Lys Thr Asn Leu Glu Ile Ile Ile Leu
                755                 760                 765
Val Gly Thr Ala Val Ile Ala Met Phe Phe Trp Leu Leu Leu Val Ile
770                 775                 780
Ile Leu Arg Thr Val Lys Arg Ala Asn Gly Gly Glu Leu Lys Thr Gly
785                 790                 795                 800
Tyr Leu Ser Ile Val Met Asp Pro Asp Glu Leu Pro Leu Asp Glu His
                805                 810                 815
Cys Glu Arg Leu Pro Tyr Asp Ala Ser Lys Trp Glu Phe Pro Arg Asp
                820                 825                 830
Arg Leu Lys Leu Gly Lys Pro Leu Gly Arg Gly Ala Phe Gly Gln Val
                835                 840                 845
Ile Glu Ala Asp Ala Phe Gly Ile Asp Lys Thr Ala Thr Cys Arg Thr
850                 855                 860
Val Ala Val Lys Met Leu Lys Glu Gly Ala Thr His Ser Glu His Arg
865                 870                 875                 880
Ala Leu Met Ser Glu Leu Lys Ile Leu Ile His Ile Gly His His Leu
                885                 890                 895
Asn Val Val Asn Leu Leu Gly Ala Cys Thr Lys Pro Gly Gly Pro Leu
                900                 905                 910
Met Val Ile Val Glu Phe Cys Lys Phe Gly Asn Leu Ser Thr Tyr Leu
                915                 920                 925
Arg Ser Lys Arg Asn Glu Phe Val Pro Tyr Lys Thr Lys Gly Ala Arg
            930                 935                 940
Phe Arg Gln Gly Lys Asp Tyr Val Gly Ala Ile Pro Val Asp Leu Lys
945                 950                 955                 960
Arg Arg Leu Asp Ser Ile Thr Ser Ser Gln Ser Ser Ala Ser Ser Gly
                    965                 970                 975
Phe Val Glu Glu Lys Ser Leu Ser Asp Val Glu Glu Glu Glu Ala Pro
                980                 985                 990
Glu Asp Leu Tyr Lys Asp Phe Leu Thr Leu Glu His Leu Ile Cys Tyr
            995                 1000                1005
Ser Phe Gln Val Ala Lys Gly Met Glu Phe Leu Ala Ser Arg Lys
            1010                1015                1020
```

-continued

```
Cys Ile His Arg Asp Leu Ala Ala Arg Asn Ile Leu Leu Ser Glu
    1025            1030                1035
Lys Asn Val Val Lys Ile Cys Asp Phe Gly Leu Ala Arg Asp Ile
    1040            1045                1050
Tyr Lys Asp Pro Asp Tyr Val Arg Lys Gly Asp Ala Arg Leu Pro
    1055            1060                1065
Leu Lys Trp Met Ala Pro Glu Thr Ile Phe Asp Arg Val Tyr Thr
    1070            1075                1080
Ile Gln Ser Asp Val Trp Ser Phe Gly Val Leu Leu Trp Glu Ile
    1085            1090                1095
Phe Ser Leu Gly Ala Ser Pro Tyr Pro Gly Val Lys Ile Asp Glu
    1100            1105                1110
Glu Phe Cys Arg Arg Leu Lys Glu Gly Thr Arg Met Arg Ala Pro
    1115            1120                1125
Asp Tyr Thr Thr Pro Glu Met Tyr Gln Thr Met Leu Asp Cys Trp
    1130            1135                1140
His Gly Glu Pro Ser Gln Arg Pro Thr Phe Ser Glu Leu Val Glu
    1145            1150                1155
His Leu Gly Asn Leu Leu Gln Ala Asn Ala Gln Gln Asp Gly Lys
    1160            1165                1170
Asp Tyr Ile Val Leu Pro Ile Ser Glu Thr Leu Ser Met Glu Glu
    1175            1180                1185
Asp Ser Gly Leu Ser Leu Pro Thr Ser Pro Val Ser Cys Met Glu
    1190            1195                1200
Glu Glu Glu Val Cys Asp Pro Lys Phe His Tyr Asp Asn Thr Ala
    1205            1210                1215
Gly Ile Ser Gln Tyr Leu Gln Asn Ser Lys Arg Lys Ser Arg Pro
    1220            1225                1230
Val Ser Val Lys Thr Phe Glu Asp Ile Pro Leu Glu Glu Pro Glu
    1235            1240                1245
Val Lys Val Ile Pro Asp Asp Asn Gln Thr Asp Ser Gly Met Val
    1250            1255                1260
Leu Ala Ser Glu Glu Leu Lys Thr Leu Glu Asp Arg Thr Lys Leu
    1265            1270                1275
Ser Pro Ser Phe Gly Gly Met Val Pro Ser Lys Ser Arg Glu Ser
    1280            1285                1290
Val Ala Ser Glu Gly Ser Asn Gln Thr Ser Gly Tyr Gln Ser Gly
    1295            1300                1305
Tyr His Ser Asp Asp Thr Asp Thr Thr Val Tyr Ser Ser Glu Glu
    1310            1315                1320
Ala Glu Leu Leu Lys Leu Ile Glu Ile Gly Val Gln Thr Gly Ser
    1325            1330                1335
Thr Ala Gln Ile Leu Gln Pro Asp Ser Gly Thr Thr Leu Ser Ser
    1340            1345                1350
Pro Pro Val
    1355
```

METHOD OF TREATING EPITHELIAL GROWTH FACTOR RECEPTOR (EGFR) T790M-POSITIVE NON-SMALL CELL LUNG CANCER BY ADMINISTERING A COMBINATION OF A VEGFR-2 ANTIBODY AND OSIMERTINIB

The present invention relates to a combination of anti-human VEGFR-2 antibodies and EGFR tyrosine kinase inhibitors for the treatment of T790M-positive EGFR-mutant non-small cell lung cancer.

Epidermal growth factor receptor (EGFR) tyrosine kinse inhibitors (TKIs) typically prolong the progression-free survival of patients with metastatic non-small cell lung cancer (NSCLC) whose tumors display activating mutation(s) in the EGFR gene. However, many such patients eventually develop resistance to EGFR TKIs after treatment. One important mechanism of acquired resistance is the T790M EGFR mutation in exon 20 of the EGFR gene. This acquired resistance has led to the development of further TKIs such as osimertinib. Osimertinib 80-mg once-daily table has been approved in the United States and the European Union for the treatment of patients with metastic EGFR T790M mutation-positive NSCLC, who have progressed on or after EGFR TKI therapy. However, some tumours may develop further resistance and thus a need exists for additional treatments for overcoming these resistance mechanisms.

The first generation TKI, erlotinib, in combination with bevacizumab has been shown to improve progression free survival, but not overall survival, in patients who have previously received a first-line chemotherapy regimen for the treatment of NSCLC (Johnson, B. E., et al., *Journal of Clinical Oncology* 2013; 31 (31): 3926-3934). RELAY, a Phase 3 randomized study of erlotinib with or without ramucirumab as first-line therapy for patients with EGFR-mutant NSCLC is also ongoing (NCT02411448).

The inventions described herein derive, in part, from Study I4T-MC-JVDL, an open-label, multicenter Phase 1 study with expansion cohorts to evaluate the safety and preliminary efficacy of ramucirumab in combination with osimertinib.

Osimertinib is a third-generation EGFR inhibitor with selectivity against certain mutant forms of EGFR. Osimertinib may be useful for the treatment of cancers which are, or have become, resistant to treatment with the EGFR inhibitors: gefinitib, erlotinib, and/or afatinib. Osimertinib has the structure:

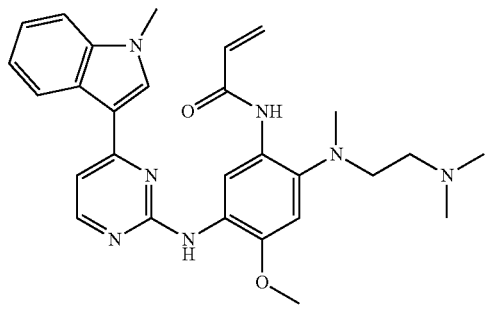 [SMILES: C=CC(=O)Nc1cc(Nc2nccc(-c3cn(C)c4ccccc34)n2)c(OC)cc1N(C)CCN(C)C]

and may be known by the chemical name: N-(2-{2-dimethylaminoethyl-methylamino}-4-methoxy-5-{[4-(1-methylindol-3-yl)pyrimidin-2-yl]amino}phenyl)prop-2-enamide. Osimertinib and pharmaceutically acceptable salts thereof are disclosed in WO2013/014448. A non-limiting example of a pharmaceutically acceptable salt of osimertinib is a mesylate salt. A non-limiting example of osimertinib is TAGRISSO®.

Ramucirumab is an anti-human VEGFR-2 antibody produced in mammalian cells, wherein the antibody comprises two light chains, each of the light chains having the amino acid sequence of SEQ ID NO: 3, and two heavy chains, each of the heavy chains having the amino acid sequence of SEQ ID NO: 4. The light chain variable region of ramucirumab is that given in SEQ ID NO: 1. The heavy chain variable region of ramucirumab is that given in SEQ ID NO: 2. A non-limiting example of ramucirumab is CYRAlVlZA®. Ramucirumab is a human IgG1 monoclonal antibody directed against human vascular endothelial growth factor receptor 2 (VEGFR-2). Ramucirumab and methods of making and using ramucirumab are disclosed in WO2003/075840.

As used herein, the term "human VEGFR-2" refers to Human Vascular Endothelial Growth Factor Receptor 2, having the amino acid sequence of SEQ ID NO: 5. VEGFR-2 is also known as KDR.

As used herein, the term "human EGFR" refers to human epidermal growth factor receptor.

As used herein, "about" means a deviation from a given value by no more or less than 10%, by weight. As a non-limiting example, "about 100 mg" denotes a range from 90 mg (inclusive) to 110 mg (inclusive).

The term "antibody" as used herein refers to a polypetide complex having two heavy chains (HC) and two lights chains (LC) such that the heavy chains and light chains are interconnected by disulfide bonds; wherein the antibody is an IgG subclass antibody.

As used herein, the term "light chain variable region" or "LCVR" refers to a portion of a light chain of an antibody molecule that includes the amino acid sequences of the complementarity-determining regions ("CDRs") and framework regions (FRs).

As used herein, the term "heavy chain variable region" or "HCVR" refers to a portion of a heavy chain of an antibody molecule that includes the amino acid sequences of the CDRs and FRs.

As used herein, the terms "treating," "treat," or "treatment" refer to restraining, slowing, lessening, reducing, or reversing the progression or severity of an existing symptom, disorder, condition, or disease, or ameliorating clinical symptoms of a condition. Beneficial or desired clinical results include, but are not limited to, alleviation of symptoms, diminishment of the extent of a disease or disorder, stabilization of a disease or disorder (i.e., where the disease or disorder does not worsen), delay or slowing of the progression of a disease or disorder, amelioration or palliation of the disease or disorder, and remission (whether partial or total) of the disease or disorder, whether detectable or undetectable. Treatment can also mean prolonging survival as compared to expected survival if not receiving treatment. Those in need of treatment include those already with the disease. In some examples, the present invention can be used as a medicament.

As used herein, the term "patient" refers to a mammal, preferably a human.

As used herein, the term "cancer" refers to or describes the physiological condition in patients that is typically characterized by unregulated cellular proliferation. Included in this definition are benign and malignant cancers.

Currently approved tests for EGFR T790M-positive NSCLC that are currently recommended for the use of osimertinib include those listed below. In the US, as approved by the Food and Drug Administration, the Cobas®

EGFR Mutation Test Version 2 is a real-time polymerase chain reaction test for the qualitative detection of defined mutations of the EGFR gene in DNA derived from formalin-fixed paraffin-embedded tumor tissue from NSCLC patients. The test is intended to aid in identifying patients with NSCLC whose tumors have defined EGFR mutations and for whom safety and efficacy of a drug have been established as follows: (a) Tarceva® (erlotinib)—Exon 19 deletions and L858R mutations and (b) Tagrisso® (osimertinib)—T790M mutations. In the EU, according to the currently approved Summary of Product Characteristics (SmPC) for osimertinib as a treatment for locally advanced or metastatic NSCLC, a validated test is recommended to determine EGFR T790M mutation status. As indicated in the SmPC, the mutation status should be tested using either tumor DNA derived from a tissue sample or circulating tumor DNA (ctDNA) obtained from a plasma sample. Only robust, reliable, and sensitive tests with demonstrated utility for the determination of T790M mutation status of tumor-derived DNA (from a tissue or a plasma sample) should be used. Positive determination of T790M mutation status using either a tissue-based or plasma-based test indicates eligibility for treatment with osimertinib. If a plasma-based ctDNA test is used and the result is negative, it is advisable to follow-up with a tissue test wherever possible due to the potential for false negative results using a plasma-based test.

The presence of the EGFR activating mutations such as the deletion of exon 19 and the L858R mutation in exon 21 can be determined by known methods, a non-limiting example of which is the Cobas® EGFR Mutation Test v2 (Roche Molecular Diagnostics).

The study population for Study I4T-MC-JVDL is as follows. Patients are eligible to be included in the study only if they meet all of the following criteria: [1] Have a diagnosis of NSCLC with at least 1 measurable lesion assessable using standard techniques by the Response Evaluation Criteria In Solid Tumors Version 1.1 (Eisenhauer, E. A. et al., *Eur. J. Cancer:* 2009; 45(2): 228-247); [2] Have locally advanced or metastatic NSCLC not amenable to curative therapy; [3] Have lung cancer with documented evidence of one of the 2 common EGFR mutations known to be associated with EGFR TKI sensitivity (Ex19del, L858R); [4] Have disease progression immediately following first-line EGFR TKI treatment (with disease control as the best response to the first-line EGFR TKI treatment) regardless of prior chemotherapy; [5] Have T790M-positive status using a test validated and performed locally after disease progression on EGFR TKI treatment; [6] Tumor tissue from a biopsy taken after disease progression on the most recent EGFR TKI treatment is required. Patients for whom newly obtained samples cannot be obtained (for example, inaccessible or patient safety concern) may submit an archived specimen only upon agreement from the Sponsor; [7] Have Eastern Cooperative Oncology Group Performance Status of 0 or 1 at the time of enrollment (Oken, M. M. et al., *Am. J. Clin. Oncol.* 1982; 5:649-655); [8] Have provided signed informed consent and are amenable to compliance with protocol schedules and testing; [9] Have serum albumin that is ≥25 g/L at the time of enrollment; [10] Have urinary protein that is <2+ on dipstick or routine urinalysis. If urine dipstick or routine analysis indicates proteinuria ≥2+, then a 24-hour urine must be collected and must demonstrate <2 g of protein in 24 hours to allow participation in the study; [11] Have adequate organ function with all screening labs performed within 7 days of treatment initiation; [12] Be at least 18 years old at the time of signing informed consent; [13] Have a life expectancy of ≥3 months; [14] Have resolution, except where otherwise stated in the inclusion criteria, of all clinically significant toxic effects of prior systemic cancer therapy, surgery, or radiotherapy to Grade ≤1 by NCI CTCAE Version 4.0; [15] For male patients, are sterile (including vasectomy confirmed by postvasectomy semen analysis) or agree to use a highly effective method of contraception, and to not donate sperm starting with the first dose of study therapy, during the study, and for at least 6 months following the last dose of study therapy or country requirements, whichever is longer; [16] For female patients, are surgically sterile, postmenopausal, or agree to use a highly effective method of contraception during the study, and for 6 months following the last dose of study treatment or country requirements, whichever is longer; [17] For female patients and of child-bearing potential, must have a negative serum or urine pregnancy test within 7 days prior to enrollment, and should not be breast feeding.

For the Study I4T-MC-JVDL, paients will be excluded from the study if they meet any of the following criteria: [18] Previous treatment with an EGFR mAb (except for past treatment for squamous cell carcinoma of head and neck or mCRC); [19] Previous treatment with an EGFR TKI (for example, erlotinib or gefitinib) within 8 days or approximately 5× half-life, whichever is longer, of the first dose of study treatment (If sufficient wash-out time has not occurred due to schedule or PK properties, an alternative appropriate wash-out time based on known duration and time to reversibility of drug-related AEs could be agreed upon by the Sponsor and the investigator); [20] Previous treatment with osimertinib or other third-generation EGFR TKIs; [21] Patients with symptomatic or growing brain metastases less than 4 weeks prior to enrollment. Patients with asymptomatic and stable brain metastases, such as those who have completed radiotherapy for brain metastases at least 4 weeks prior to receiving treatment and requiring no steroids or anticonvulsants for at least 2 weeks prior to receiving treatment, are eligible; [22] Have a serious concomitant illness or medical condition(s) including, but not limited to, the following: Active infection including hepatitis B, hepatitis C, and human immunodeficiency virus (HIV) infection (screening for chronic conditions is not required), active or uncontrolled clinically serious infection, active substance abuse disorders, history of drug-induced interstitial lung disease (ILD), ILD, or radiation pneumonitis requiring treatment with steroid prior to study enrollment, or any evidence of clinically active ILD, known allergy or hypersensitivity reaction to any of the treatment components; [23] Have history of another malignancy in 3 years, EXCEPT: adequately treated nonmelanomatous skin cancer, curatively treated cervical carcinoma in situ, other noninvasive carcinoma or in situ neoplasm, or prostate cancer that is not expected to impact patient survival; [24] Have a significant bleeding disorder or vasculitis or had a Grade ≥3 bleeding episode within 12 weeks prior to enrollment. Patients with a history of gross hemoptysis (defined as bright red blood of ≥½ teaspoon) within 2 month prior to enrollment are excluded; [25] Have experienced any arterial thrombotic event or arterial thromboembolic event, including myocardial infarction, unstable angina (history or evidence of current clinically relevant coronary artery disease of current ≥Class III as defined by Canadian Cardiovascular Society Angina Grading Scale or congestive heart failure of current ≥Class III as defined by the New York Heart Association), cerebrovascular accident, or transient ischemic attack, within 6 months prior to enrollment; [26] Have a history of deep vein thrombosis, pulmonary embolism, or any other significant venous thromboembolism (venous catheter thrombosis or superficial venous thrombosis not considered "significant") during the 3 months prior to study enrollment. Patients with venous thromboembolism occurring 3 to 6 months prior to study enrollment are allowed, if being treated with low molecular weight heparin; [27] Have a history of GI perforation and/or fistula within 6 months prior to Enrollment; [28] Have a bowel obstruction, history or presence of inflammatory enteropathy or extensive intestinal resection (hemicolectomy or extensive small intestine resection with chronic diarrhea), Crohn's disease, ulcerative colitis, or chronic diarrhea; [29] Have uncontrolled hypertension, as defined in CTCAE Version 4.0, prior to initiating study treatment, despite antihypertensive intervention. CTCAE Version 4.0 defines uncontrolled hypertension as Grade >2 hypertension; clinically, the patient continues to experience elevated blood pressure (systolic >160 mmHg and/or diastolic >100 mmHg) despite medications; [30] Are receiving chronic therapy with any of the following medications within 7 days prior to enrollment: a. nonsteroidal anti-inflammatory agents (NSAIDs; such as indomethacin, ibuprofen, naproxen, or similar agents) b. other antiplatelet agents (such as clopidogrel, ticlopidine, dipyridamole, or anagrelide) Aspirin use at doses up to 325 mg/day is permitted; [31] Have had a serious or non-healing wound, ulcer, or bone fracture within 28 days prior to enrollment; [32] Have an elective or a planned major surgery during the course of the trial; [33] Have undergone major surgery within 28 days prior to enrollment, or minor surgical procedure such as central venous access device placement within 7 days prior to enrollment; [34] Are currently enrolled in, or discontinued within the last 30 days from, a clinical trial involving an investigational product or any other type of medical research judged not to be scientifically or medically compatible with this study (except in the setting of EGFR TKI as detailed above). Patients participating in surveys or observational studies are eligible to participate in this study; [35] Are pregnant, or breastfeeding [36] Have radiologically documented evidence of major blood vessel invasion or encasement by cancer; [37] Have radiographic evidence of pulmonary intratumor cavitation, regardless of tumor histology; [38] Are receiving concurrent treatment with other anticancer therapy, including other chemotherapy, immunotherapy, hormonal therapy, chemoembolization, or targeted therapy or radiotherapy treatment to more than 30% of the bone marrow or with a wide field of radiation within 4 weeks prior to enrollment (except in the setting of EGFR TKI as detailed above); [39] Are currently receiving (or unable to stop use at least 1 week prior to receiving the first dose of osimertinib) medications or herbal supplements known to be potent inducers of CYP3A4; [40] Have any of the following cardiac abnormal findings: Mean resting corrected QT interval (QTc) >470 msec obtained from 3 electrocardiograms (ECGs), using the screening clinic ECG machine-derived QTc value, any clinically important abnormalities in rhythm, conduction, or morphology of resting ECG; for example, complete left bundle branch block, third-degree heart block, or second-degree heart block, any factors that increase the risk of QTc prolongation or risk of arrhythmic events such as heart failure, hypokalemia, congenital long QT syndrome, family history of long QT syndrome or unexplained sudden death under 40 years of age in first-degree relatives, or any concomitant medication known to prolong the QT interval, have a history of any of the following conditions: presyncope or syncope of either unexplained or cardiovascular etiology, ventricular arrhythmia (including but not limited to ventricular tachycardia and ventricular fibrillation), or sudden cardiac arrest; [41] Have undergone chest irradiation within 2 weeks prior to study drug administration, have not recovered from all radiation-related toxicities, or requires corticosteroids. A 2-week washout is permitted for focal palliative radiation to non-central nervous system disease; [42] Have refractory nausea and vomiting, inability to swallow the formulated product, or previous significant bowel resection that would preclude absorption; [43] Have any other serious uncontrolled medical disorders or psychological conditions that would, in the opinion of the investigator, limit the patient's ability to complete the study or sign an informed consent document; [44] Have liver cirrhosis at a level of Child-Pugh B (or worse) or liver cirrhosis (any degree) and a history of hepatic encephalopathy or clinical meaningful ascites resulting from cirrhosis.

Ramucirumab and osimertinib will be administered as follows. Ramucirumab may be administered at a dose of 10 mg/kg via intravenous administration over 60 minutes on Day 1 of a two-week cycle in combination with 80 mg of osimertinib administered once daily. A patient may continue to receive ramucirumab in combination with osimertinib at the assigned dose level until he/she meets one or more of the specified reasons for discontinuation such as the observation of a dose-limiting toxicity.

The ramucirumab dose may be delayed and/or reduced to 8 mg/kg if the patient experiences an adverse event. Doses may be delayed to allow time for the patient to recover from the event. Certain adverse events require immediate and permanent discontinuation of study treatment. If administration of ramucirumab is delayed for more than 4 weeks (2 cycles) after Day 1 of the most recent treatment cycle, the patient should be discontinued from ramucirumab treatment. Any patient who requires a dose reduction to less than 6 mg/kg of ramucirumab will have ramucirumab discontinued. Such patients may continue with osimertinib as a single agent.

ORR (objective response rate) and DCR (disease control rate) (according to RECIST 1.1), and the corresponding confidence intervals, will be provided for each cohort, respectively. Time-to-event variables, such as time to response, DOR (duration of response), PFS (progression free survival), and OS (overall survival), will be estimated by Kaplan-Meier methodology for each cohort, respectively. Presentations of efficacy may include patients enrolled in the Dose-Finding Portion with the same treatment schedule. All patients who receive at least 1 dose of ramucirumab or osimertinib will be evaluated for safety and toxicity. Adverse event (AE) terms and severity grades will be assigned by the investigator using CTCAE Version 4.0. Safety analyses will include summaries of the following: (a) DLTs: the number of patients who experienced any DLTs during DLT observation period will be summarized by dose schedule in the Dose-Finding Portion for each arm; (b) AEs, including severity and possible relationship to study drug; c) AEs by Medical Dictionary for Regulatory Activities® System Organ Class (SOC) by decreasing frequency of Preferred Term within SOC; (d) Laboratory and nonlaboratory AEs by CTCAE term and maximum CTCAE grade (regardless of causality and at least possibly related to study treatment).

The objective response rate (ORR) is the proportion of enrolled patients who have received any amount of either study drug, have at least 1 postbaseline tumor image, and achieve a best overall response of complete response (CR) or partial response (PR).

Duration of response (DOR) is defined only for responders (patients with a confirmed CR or PR). It is measured from the date of first evidence of a confirmed CR or PR to the date of objective progression or the date of death due to any cause, whichever is earlier. If a responder is not known to have died or have objective progression as of the data inclusion cutoff date, DOR will be censored at the date of the last complete objective progression-free disease assessment.

Disease Control Rate (DCR) is defined as the proportion of enrolled patients who have a best overall response of CR, PR, or stable disease. Progression-free survival (PFS) is defined as the time from the date of first study treatment until the date of the first observed radiographically documented PD or death due to any cause, whichever is earlier. The censoring is taken in the following order: —if a patient does not have a complete baseline disease assessment, then the PFS time will be censored at the enrollment date, regardless of whether or not objectively determined disease progression or death has been observed for the patient; otherwise, —if a patient is not known to have died or have objective progression as of the data inclusion cutoff date for the analysis, the PFS time will be censored at the last complete objective progression-free disease assessment date. ORR, DOR, DCR, and PFS will be assessed based on RECIST 1.1 (Eisenhauer, E. A. et al., *Eur. J. Cancer:* 2009; 45(2): 228-247).

Overall survival (OS), including 1- and 2-year survival rates, is determined from the date of first study treatment until death due to any cause. If the patient was alive at the data inclusion cutoff date for the analysis (or was lost to follow-up), OS will be censored on the last date the patient was known to be alive.

The present disclosure provides a method of treating advanced or metastatic EGFR T790M-positive non-small cell lung cancer in a human patient comprising administering to the patient an antibody comprising a heavy chain having a heavy chain variable region having the amino acid sequence of SEQ ID NO: 2 and a light chain having a light chain variable region having the amino acid sequence of SEQ ID NO: 1 at a dose of about 6 mg/kg to about 10 mg/kg on day 1 of a 14 day cycle, in combination with osimertinib or a pharmaceutically acceptable salt thereof administered orally at a daily dose of about 40 mg to about 80 mg.

The present disclosure provides a method of treating advanced or metastatic EGFR T790M-positive non-small cell lung cancer in a human patient comprising administering to the patient an antibody comprising a heavy chain having a heavy chain variable region having the amino acid sequence of SEQ ID NO: 2 and a light chain having a light chain variable region having the amino acid sequence of SEQ ID NO: 1 at a dose of about 6 mg/kg to about 10 mg/kg on day 1 of a 14 day cycle, in combination with osimertinib or a pharmaceutically acceptable salt thereof administered orally at a daily dose of about 40 mg to about 80 mg; wherein the heavy chain has the amino acid sequence of SEQ ID NO: 4 and the light chain has the amino acid sequence of SEQ ID NO: 3.

The present disclosure provides a method of treating advanced or metastatic EGFR T790M-positive non-small cell lung cancer in a human patient comprising administering to the patient an antibody comprising a heavy chain having a heavy chain variable region having the amino acid sequence of SEQ ID NO: 2 and a light chain having a light chain variable region having the amino acid sequence of SEQ ID NO: 1 at a dose of about 6 mg/kg to about 10 mg/kg on day 1 of a 14 day cycle, in combination with osimertinib or a pharmaceutically acceptable salt thereof administered orally at a daily dose of about 40 mg to about 80 mg; wherein the antibody is administered by intravenous administration.

The present disclosure provides a method of treating advanced or metastatic EGFR T790M-positive non-small cell lung cancer in a human patient comprising administering to the patient an antibody comprising a heavy chain having a heavy chain variable region having the amino acid sequence of SEQ ID NO: 2 and a light chain having a light chain variable region having the amino acid sequence of SEQ ID NO: 1 at a dose of about 6 mg/kg to about 10 mg/kg on day 1 of a 14 day cycle, in combination with osimertinib or a pharmaceutically acceptable salt thereof administered orally at a daily dose of about 40 mg to about 80 mg; wherein the patient has previously received treatment with gefitinib, erlotinib, or afatinib prior to receiving the antibody.

The present disclosure provides a method of treating advanced or metastatic EGFR T790M-positive non-small cell lung cancer in a human patient comprising administering to the patient an antibody comprising a heavy chain having a heavy chain variable region having the amino acid sequence of SEQ ID NO: 2 and a light chain having a light chain variable region having the amino acid sequence of SEQ ID NO: 1 at a dose of about 6 mg/kg to about 10 mg/kg on day 1 of a 14 day cycle, in combination with osimertinib or a pharmaceutically acceptable salt thereof administered orally at a daily dose of about 40 mg to about 80 mg; wherein the cancer further comprises at least one additional EGFR activating mutation selected from the group consisting of a deletion of exon 19 and a L858R mutation in exon 21.

The present disclosure provides a method of treating advanced or metastatic EGFR T790M-positive non-small cell lung cancer in a human patient comprising administering to the patient an antibody comprising a heavy chain having a heavy chain variable region having the amino acid sequence of SEQ ID NO: 2 and a light chain having a light chain variable region having the amino acid sequence of SEQ ID NO: 1 at a dose of 6 mg/kg to 10 mg/k on day 1 of a 14 day cycle, in combination with osimertinib or a pharmaceutically acceptable salt thereof administered orally at a daily dose of about 40 mg to about 80 mg.

The present disclosure provides a method of treating advanced or metastatic EGFR T790M-positive non-small cell lung cancer in a human patient comprising administering to the patient an antibody comprising a heavy chain having a heavy chain variable region having the amino acid sequence of SEQ ID NO: 2 and a light chain having a light chain variable region having the amino acid sequence of SEQ ID NO: 1 at a dose of 6 mg/kg to 10 mg/kg on day 1 of a 14 day cycle, in combination with osimertinib or a pharmaceutically acceptable salt thereof administered orally at a daily dose of about 40 mg to about 80 mg.

The present disclosure provides a method of treating advanced or metastatic EGFR T790M-positive non-small cell lung cancer in a human patient comprising administering to the patient an antibody comprising a heavy chain having a heavy chain variable region having the amino acid sequence of SEQ ID NO: 2 and a light chain having a light chain variable region having the amino acid sequence of SEQ ID NO: 1 at a dose of about 8 mg/kg to about 10 mg/kg on day 1 of a 14 day cycle, in combination with osimertinib or a pharmaceutically acceptable salt thereof administered orally at a daily dose of about 40 mg to about 80 mg.

The present disclosure provides a method of treating advanced or metastatic EGFR T790M-positive non-small cell lung cancer in a human patient comprising administering to the patient an antibody comprising a heavy chain having a heavy chain variable region having the amino acid sequence of SEQ ID NO: 2 and a light chain having a light chain variable region having the amino acid sequence of SEQ ID NO: 1 at a dose of about 8 mg/kg to 10 mg/kg on day 1 of a 14 day cycle, in combination with osimertinib or a pharmaceutically acceptable salt thereof administered orally at a daily dose of about 40 mg to about 80 mg.

The present disclosure provides a method of treating advanced or metastatic EGFR T790M-positive non-small cell lung cancer in a human patient comprising administering to the patient an antibody comprising a heavy chain having a heavy chain variable region having the amino acid sequence of SEQ ID NO: 2 and a light chain having a light chain variable region having the amino acid sequence of SEQ ID NO: 1 at a dose of about 6 mg/kg on day 1 of a 14 day cycle, combination with osimertinib or a pharmaceutically acceptable salt thereof administered orally at a daily dose of about 40 mg to about 80 mg.

The present disclosure provides a method of treating advanced or metastatic EGFR T790M-positive non-small cell lung cancer in a human patient comprising administering to the patient an antibody comprising a heavy chain having a heavy chain variable region having the amino acid sequence of SEQ ID NO: 2 and a light chain having a light chain variable region having the amino acid sequence of SEQ ID NO: 1 at a dose of 6 mg/kg on day 1 of a 14 day cycle, in combination with osimertinib or a pharmaceutically acceptable salt thereof administered orally at a daily dose of about 40 mg to about 80 mg.

The present disclosure provides a method of treating advanced or metastatic EGFR T790M-positive non-small cell lung cancer in a human patient comprising administering to the patient an antibody comprising a heavy chain having a heavy chain variable region having the amino acid sequence of SEQ ID NO: 2 and a light chain having a light chain variable region having the amino acid sequence of SEQ ID NO: 1 at a dose of about 8 mg/kg on day 1 of a 14 day cycle, in combination with osimertinib or a pharmaceutically acceptable salt thereof administered orally at a daily dose of about 40 mg to about 80 mg.

The present disclosure provides a method of treating advanced or metastatic EGFR T790M-positive non-small cell lung cancer in a human patient comprising administering to the patient an antibody comprising a heavy chain having a heavy chain variable region having the amino acid sequence of SEQ ID NO: 2 and a light chain having a light chain variable region having the amino acid sequence of SEQ ID NO: 1 at a dose of 8 mg/kg on day 1 of a 14 day cycle, in combination with osimertinib or a pharmaceutically acceptable salt thereof administered orally at a daily dose of about 40 mg to about 80 mg.

The present disclosure provides a method of treating advanced or metastatic EGFR T790M-positive non-small cell lung cancer in a human patient comprising administering to the patient an antibody comprising a heavy chain having a heavy chain variable region having the amino acid sequence of SEQ ID NO: 2 and a light chain having a light chain variable region having the amino acid sequence of SEQ ID NO: 1 at a dose of about 10 mg/kg on day 1 of a 14 day cycle, in combination with osimertinib or a pharmaceutically acceptable salt thereof administered orally at a daily dose of about 40 mg to about 80 mg.

The present disclosure provides a method of treating advanced or metastatic EGFR T790M-positive non-small cell lung cancer in a human patient comprising administering to the patient an antibody comprising a heavy chain having a heavy chain variable region having the amino acid sequence of SEQ ID NO: 2 and a light chain having a light chain variable region having the amino acid sequence of SEQ ID NO: 1 at a dose of 10 mg/kg on day 1 of a 14 day cycle, in combination with osimertinib or a pharmaceutically acceptable salt thereof administered orally at a daily dose of about 40 mg to about 80 mg.

The present disclosure provides a method of treating advanced or metastatic EGFR T790M-positive non-small cell lung cancer in a human patient comprising administering to the patient an antibody comprising a heavy chain having a heavy chain variable region having the amino acid sequence of SEQ ID NO: 2 and a light chain having a light chain variable region having the amino acid sequence of SEQ ID NO: 1 at a dose of about 6 mg/kg to about 10 mg/kg on day 1 of a 14 day cycle, in combination with osimertinib or a pharmaceutically acceptable salt thereof administered orally at a daily dose of about 80 mg.

The present disclosure provides a method of treating advanced or metastatic EGFR T790M-positive non-small cell lung cancer in a human patient comprising administering to the patient an antibody comprising a heavy chain having a heavy chain variable region having the amino acid sequence of SEQ ID NO: 2 and a light chain having a light chain variable region having the amino acid sequence of SEQ ID NO: 1 at a dose of about 6 mg/kg to about 10 mg/kg on day 1 of a 14 day cycle, in combination with osimertinib or a pharmaceutically acceptable salt thereof administered orally at a daily dose of 80 mg.

The present disclosure provides a method of treating advanced or metastatic EGFR T790M-positive non-small cell lung cancer in a human patient comprising administering to the patient an antibody comprising a heavy chain having a heavy chain variable region having the amino acid sequence of SEQ ID NO: 2 and a light chain having a light chain variable region having the amino acid sequence of SEQ ID NO: 1 at a dose of about 6 mg/kg to about 10 mg/kg on day 1 of a 14 day cycle, in combination with osimertinib or a pharmaceutically acceptable salt thereof administered orally at a daily dose of about 40 mg.

The present disclosure provides a method of treating advanced or metastatic EGFR T790M-positive non-small cell lung cancer in a human patient comprising administering to the patient an antibody comprising a heavy chain having a heavy chain variable region having the amino acid sequence of SEQ ID NO: 2 and a light chain having a light chain variable region having the amino acid sequence of SEQ ID NO: 1 at a dose of about 6 mg/kg to about 10 mg/kg on day 1 of a 14 day cycle, in combination with osimertinib or a pharmaceutically acceptable salt thereof administered orally at a daily dose of 40 mg.

The present disclosure provides a method of treating advanced or metastatic EGFR T790M-positive non-small cell lung cancer in a human patient comprising administering to the patient an antibody comprising a heavy chain having a heavy chain variable region having the amino acid sequence of SEQ ID NO: 2 and a light chain having a light chain variable region having the amino acid sequence of SEQ ID NO: 1 at a dose of about 6 mg/kg to about 10 mg/kg on day 1 of a 14 day cycle, in combination with osimertinib or a pharmaceutically acceptable salt thereof administered orally at a daily dose of about 40 mg to about 80 mg; wherein the patient is administered a mesylate salt of osimertinib.

The present disclosure provides a method of treating advanced or metastatic EGFR T790M-positive non-small cell lung cancer in a human patient comprising administering to the patient ramucirumab at a dose of about 6 mg/kg to about 10 mg/kg on day 1 of a 14 day cycle, in combination with osimertinib or a pharmaceutically acceptable salt thereof administered orally at a daily dose of about 40 mg to about 80 mg; optionally, wherein the cancer further comprises at least one additional EGFR activating mutation selected from the group consisting of a deletion of exon 19 and an a L858R mutation in exon 21.

The present disclosure provides a method of treating advanced or metastatic EGFR T790M-positive non-small cell lung cancer in a human patient comprising administering to the patient ramucirumab at a dose of about 8 mg/kg to about 10 mg/kg on day 1 of a 14 day cycle, in combination with osimertinib or a pharmaceutically acceptable salt thereof administered orally at a daily dose of about 40 mg to about 80 mg; optionally, wherein the cancer further comprises at least one additional EGFR activating mutation selected from the group consisting of a deletion of exon 19 and an a L858R mutation in exon 21.

The present disclosure provides a method of treating advanced or metastatic EGFR T790M-positive non-small cell lung cancer in a human patient comprising administering to the patient ramucirumab at a dose of about 8 mg/kg to about 10 mg/kg on day 1 of a 14 day cycle, in combination with osimertinib or a pharmaceutically acceptable salt thereof administered orally at a daily dose of about 80 mg; optionally, wherein the cancer further comprises at least one additional EGFR activating mutation selected from the group consisting of a deletion of exon 19 and an a L858R mutation in exon 21.

The present disclosure provides a method of treating advanced or metastatic EGFR T790M-positive non-small cell lung cancer in a human patient comprising administering to the patient ramucirumab at a dose of about 10 mg/kg on day 1 of a 14 day cycle, in combination with osimertinib or a pharmaceutically acceptable salt thereof administered orally at a daily dose of 80 mg; wherein the cancer further comprises at least one additional EGFR activating mutation selected from the group consisting of a deletion of exon 19 and an a L858R mutation in exon 21.

The present disclosure provides a method of treating advanced or metastatic EGFR T790M-positive non-small cell lung cancer in a human patient comprising an antibody comprising a heavy chain having a heavy chain variable region having the amino acid sequence of SEQ ID NO: 2 and a light chain having a light chain variable region having the amino acid sequence of SEQ ID NO: 1 in combination with osimertinib or a pharmaceutically acceptable salt thereof, wherein the cancer has metastasized to the central nervous system.

The present disclosure provides a method of treating metastatic EGFR T790M-positive non-small cell lung cancer in a human patient comprising administering to the patient ramucirumab in combination with osimertinib or a pharmaceutically acceptable salt thereof; wherein the cancer has metastasized to the central nervous system.

The present disclosure provides a method of treating metastatic EGFR T790M-positive non-small cell lung cancer in a human patient comprising administering to the patient ramucirumab in combination with osimertinib or a pharmaceutically acceptable salt thereof; wherein the cancer has metastasized to the central nervous system, wherein ramucirumab is administered at a dose of about 6 mg/kg to about 10 mg/kg on day 1 of a 14 day cycle.

The present disclosure provides a method of treating metastatic EGFR T790M-positive non-small cell lung cancer in a human patient comprising administering to the patient ramucirumab in combination with osimertinib or a pharmaceutically acceptable salt thereof; wherein the cancer has metastasized to the central nervous system, wherein osimertinib or a pharmaceutically acceptable salt thereof is administered orally at a daily dose of about 40 mg to about 80 mg.

The present disclosure provides an anti-human VEGFR-2 (SEQ ID NO: 5) antibody for use in simultaneous, separate, or sequential combination with osimertinib or a pharmaceutically acceptable salt thereof in the treatment of patients with metastatic EGFR T790M-positive non-small cell lung cancer.

The present disclosure provides an anti-human VEGFR-2 (SEQ ID NO: 5) antibody for use in simultaneous, separate, or sequential combination with osimertinib or a pharmaceutically acceptable salt thereof in the treatment of patients with metastatic EGFR T790M-positive non-small cell lung cancer; wherein the antibody comprises a heavy chain having a heavy chain variable region having the amino acid sequence of SEQ ID NO: 2 and a light chain having a light chain variable region having the amino acid sequence of SEQ ID NO: 1; wherein the cancer has metastasized to the central nervous system, alternatively wherein the antibody is ramucirumab.

The present disclosure provides the use of an anti-human VEGFR2 (SEQ ID NO:5) antibody for the manufacture of a medicament for the treatment of metastatic EGFR T790M-positive non-small cell lung cancer, wherein the medicament is to be administered simultaneously, separately, or sequentially with osimertinib or a pharmaceutically acceptable salt; wherein the cancer has metastasized to the central nervous system.

The present disclosure provides the use of an anti-human VEGFR2 (SEQ ID NO:5) antibody for the manufacture of a medicament for the treatment of metastatic EGFR T790M-positive non-small cell lung cancer, wherein the medicament is to be administered simultaneously, separately, or sequentially with osimertinib or a pharmaceutically acceptable salt; wherein the cancer has metastasized to the central nervous system; wherein the antibody comprises a heavy chain having a heavy chain variable region having the amino acid sequence of SEQ ID NO: 2 and a light chain having a light chain variable region having the amino acid sequence of SEQ ID NO: 1; wherein the cancer has metastasized to the central nervous system, alternatively wherein the antibody is ramucirumab.

In some embodiments of the invention, the patient has received treatment with gefitinib, erlotinib, or afatinib prior to receiving the antibody. In some embodiments of the invention, the cancer further comprises at least one additional EGFR activating mutation selected from the group consisting of a deletion of exon 19 and a L858R mutation in exon 21. In some embodiments of the invention, the patient is administered 6 mg/kg to 10 mg/kg of the antibody. In some embodiments of the invention, the patient is administered 8 mg/kg to 10 mg/kg of the antibody. In some embodiments of the invention, the patient is administered 6 mg/kg of the antibody. In some embodiments of the invention, the patient is administered 8 mg/kg of the antibody. In some embodiments of the invention, the patient is administered 10 mg/kg of the antibody. In some embodiments of the invention, the patient is administered 80 mg of osimertinib or a pharmaceutically acceptable salt thereof. In some embodiments of the invention, the patient is administered 40 mg of osimertinib or a pharmaceutically acceptable salt thereof. In some embodiments of the invention, the patient is administered a mesylate salt of osimertinib.

In embodiments that refer to a method of treatment as described herein, such embodiments are also further embodiments provided for the corresponding combination of anti-human VEGFR2 antibodies such as ramucirumab in combination with osimertinib and pharmaceutically acceptable salts thereof, for use in that treatment, or alternatively for the use of the combination for the manufacture of a medicament for use in that treatment.

Study Results

Eligible patients with advanced EGFR T790M-positive NSCLC and naïve to third-generation EGFR TKIs who progressed after EGFR TKI therapy were enrolled. In the dose-finding portion, following a dose de-escalation design, patients received daily oral osimertinib (80 mg) and 10 mg/kg intravenous (IV) of ramucirumab on day 1 (D1) every two weeks (Arm A). In both dose-finding and expansion portions, patients received study treatment until progressive disease or meeting discontinuation criteria. Primary objective of the study is to assess the safety and tolerability of ramucirumab combined with osimertinib, whereas secondary objectives include preliminary efficacy.

Three patients were treated in the completed dose-finding portion for the combination of ramucirumab and osimertinib. The expansion cohort for ramucirumab/osimertinib is fully enrolled with 22 patients. No dose-limiting toxicities (DLTs) have been observed. After the DLT observation period, an unrelated serious AE of Grade 2 diverticulitis (unrelated to study treatment) was observed. Expansion cohort for ramucirumab/osimertinib is fully enrolled with 22 patients. Safety data is available for 18 our of the 22 patients. Grade ≥3 TEAEs were reported in 4 patients, including dyspnea (unrelated [n=1]), decreased appetite (unrelated [n=1]), hypertension (related [n=2]). Three patients reported serious adverse events (none related to study treatment): Grade 3 dyspnea and Grade 2 pyrexia, Grade 2 dyspnea, and Grade 2 urinary tract infection. No deaths were reported in patients in the dose-finding portion, and one death unrelated to study treatment was report in the expansion cohort. The recommended dose for the expansion cohort is 10 mg/kg of ramucirumab IV every two weeks with oral 80 mg of osimertinib.

Patients (N=25) were 45-80 years (median 64) with ECOG-PS 0 (n=3) or 1 (n=22) and 10 patients had central nervous system (i.e. CNS) metastasis at enrollment while 15 never had CNS metastasis. Patients with CNS metastasis could have had prior radiotherapy (n=7) or no radiotherapy (n=3) to the CNS. Median follow-up time was 7.23 months. Fifteen patients remained on study treatment (five with CNS metastasis, ten without). TEAEs of interest (CNS metastasis, no CNS metastasis), such as headache (4/10, 5/15), vomiting (3/10, 4/15), and nausea (2/10, 4/15), were observed with comparable rates in patients with or without CNS metastasis. One patient developed TEAE of cerebral hemorrhage (Grade 1), related to CNS metastasis, but unrelated to study treatment, according to the investigator. Another patient with CNS metastasis developed Grade 5 TRAE of subdural hemorrhage, unrelated to CNS metastasis, ~7 weeks after the last dose of Ram. Only one patient with CNS metastasis had measurable CNS lesions (tumor shrinkage of 24% [SD] as best response). The other nine patients with CNS metastasis had non-measurable CNS lesions, one of whom had a CNS complete response; his systemic best response was SD. The rest of patients had CNS non-CR/non-PD. To date, one patient (1/25) developed CNS progression (due to new CNS lesion); and their CNS best response was SD. These results demonstrate that the combination of ramucirumab and osimertinib displays antitumor activity in the CNS. Patients with CNS metastasis, with/without prior radiotherapy, appeared to tolerate this combination similarly to patients without CNS metastasis.

As of Mar. 2, 2018, the safety profile of the combination of ramucirumab and osimertinib was consistent with the safety profile for each drug as a monotherapy, with no additive toxicities. Two patients died from adverse events: one death due to cadiogenic pulmonary edema reported as unrelated to study treatment and one death due to Grade 5 subdural hemorrhage reported as related to study treatment (~7 weeks after ramucirumab discontinuation). Encouraging antitumor active was demonstrated with this combination.

The tables below further summarize the results from the ongoing trial.

TABLE 1

Overview of Adverse Events

| | Ram 10 mg/kg + Osi 80 mg (N = 25) | |
|---|---|---|
| | TEAE, n (%) | TRAE, n (%) |
| Any Grade AE | 25 (100) | 25 (100) |
| Grade ≥ 3 AE | 10 (40) | 4 (16) |
| Serious AE | 8 (32) | 1 (4) |
| Discountinued study due to AE | 1 (4)$^a$ | 1 (4)$^a$ |
| AE leading to death | 1 (4)$^b$ | 0 |

Abbreviations: AE = adverse event; N = number of treated patients from the dose-finding Arm A and expansion Cohort A; Osi = osimertinib; Ram = ramucirumab; TEAE = treatment-emergent adverse event; TRAE = treatment-related adverse event.
$^a$Ram discontinued for Grade 3 congestive heart failure in a 76-year-old patient with adenocarcinoma of lung, who subsequently experienced Grade 5 subdural hemorrhage ~7 weeks after the last dose of Ram.
$^b$Death due to cardiogenic pulmonary edema reported as unrelated to study treatment.

TABLE 2

Decreased Tumor Burden in Treated Patients
Ram 10 mg/kg + Osi 80 mg (N = 25)

| | Confirmed Best Overal Response N (%) |
|---|---|
| Complete Response (CR) | 1 (4) |
| Partial Response (PR) | 18 (72) |
| Stable Disease (SD) | 4 (16) |
| Progressive Disease (PD) | 1 (4) |
| Non-evaluable | 1 (4) |
| Objective response rate (CR/PR) | 19 (76) |
| Disease control rate (CR/PR/SD) | 23 (92) |
| Median Duration of Response (90% CI) | NR (NR, NR) |
| 6-month Duration of Response Rate (90% CI) | 83.3 (62.4, 93.2) |
| 12-month Duration of Response Rate (90% CI) | 75.0 (50.9, 88.5) |

Abbreviation: NR means not reached.

TABLE 3

Progression-Free Survival
Ram 10 mg/kg + Osi 80 mg (N = 25)

| | |
|---|---|
| Patients/events | 25/10 |
| Median PFS (90% CI) | NR (5.49, NR) |
| 6-month PFS rate (90% CI) | 66.9 (48.6, 80.0) |
| 12-month PFS rate (90% CI) | 57.5 (38.9, 72.3) |
| Patients censored, n (%) | 15 (60) |

Abbreviations: N = number of treated patients from the dose-finding ARM A and expansion Cohort A; NR = not reached; PFS = progression-free survival; Osi = osimertinib; Ram = ramucirumab.

SEQUENCE LISTING
(Anti-Human VEGFR-2 Antibody, LCVR)
(Artificial Sequence)
SEQ ID NO: 1
DIQMTQSPSSVSASIGDRVTITCRASQGIDNWLGWYQQKPGKAPKWYDAS
NLDTGVPSRFSGSGSGTYFTLTISSLQAEDFAVYFCQQAKAFPPTFGGGT
KVDIK (Anti-Human VEGFR-2 Antibody, HCVR)
(Artificial Sequence)
SEQ ID NO: 2
EVQLVQSGGGLVKPGGSLRLSCAASGFTFSSYSMNWVRQAPGKGLEWVSS
ISSSSSYIYYADSVKGRFTISRDNAKNSLYLQMNSLRAEDTAVYYCARVT
DAFDIWGQGTMVTVSS (Anti-Human VEGFR-2 Antibody, LC)
(Artificial Sequence)
SEQ ID NO: 3
DIQMTQSPSSVSASIGDRVTITCRASQGIDNWLGWYQQKPGKAPKWYDAS
NLDTGVPSRFSGSGSGTYFTLTISSLQAEDFAVYFCQQAKAFPPTFGGGT
KVDIKRTVAAPSVFIFPPSDEQLKSGTASVVCLLNNFYPREAKVQWKVDN
ALQSGNSQESVTEQDSKDSTYSLSSTLTLSKADYEKHKVYACEVTHQGLS
SPVTKSFNRGEC (Anti-Human VEGFR-2 Antibody, HC)
(Artificial Sequence)
SEQ ID NO: 4
EVQLVQSGGGLVKPGGSLRLSCAASGFTFSSYSMNWVRQAPGKGLEWVSS
ISSSSSYIYYADSVKGRFTISRDNAKNSLYLQMNSLRAEDTAVYYCARVT
DAFDIWGQGTMVTVSSASTKGPSVLPLAPSSKSTSGGTAALGCLVKDYFP
EPVTVSWNSGALTSGVHTFPAVLQSSGLYSLSSVVTVPSSSLGTQTYICN
VNHKPSNTKVDKRVEPKSCDKTHTCPPCPAPELLGGPSVFLFPPKPKDTL
MISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTL
PPSREEMTKNQVSLTCLVKGFYPSDIAVEWESNGQPENNYKTTPPVLDSD
GSFFLYSKLTVDKSRWQQGNVFSCSVMHEALHNHYTQKSLSLSPGK (Human VEGFR-2) (Homo Sapiens)
SEQ ID NO: 5
MQSKVLLAVALWLCVETRAASVGLPSVSLDLPRLSIQKDILTIKANTTLQ
ITCRGQRDLDWLWPNNQSGSEQRVEVTECSDGLFCKTLTIPKVIGNDTGA
YKCFYRETDLASVIYVYVQDYRSPFIASVSDQHGVVYITENKNKTVVIPC
LGSISNLNVSLCARYPEKRFVPDGNRISWDSKKGFTIPSYMISYAGMVFC
EAKINDESYQSIMYIVVVVGYRIYDVVLSPSHGIELSVGEKLVLNCTART
ELNVGIDFNWEYPSSKHQHKKLVNRDLKTQSGSEMKKFLSTLTIDGVTRS
DQGLYTCAASSGLMTKKNSTFVRVHEKPFVAFGSGMESLVEATVGERVRI
PAKYLGYPPPEIKWYKNGIPLESNHTIKAGHVLTIMEVSERDTGNYTVIL
TNPISKEKQSHVVSLVVYVPPQIGEKSLISPVDSYQYGTTQTLTCTVYAI
PPPHHIHWYWQLEEECANEPSQAVSVTNPYPCEEWRSVEDFQGGNKIEVN
KNQFALIEGKNKTVSTLVIQAANVSALYKCEAVNKVGRGERVISFHVTRG
PEITLQPDMQPTEQESVSLWCTADRSTFENLTWYKLGPQPLPIHVGELPT
PVCKNLDTLWKLNATMFSNSTNDILIMELKNASLQDQGDYVCLAQDRKTK
KRHCVVRQLTVLERVAPTITGNLENQTTSIGESIEVSCTASGNPPPQIMW
FKDNETLVEDSGIVLKDGNRNLTIRRVRKEDEGLYTCQACSVLGCAKVEA
FFIIEGAQEKTNLEIIILVGTAVIAMFFWLLLVIILRTVKRANGGELKTG
YLSIVMDPDELPLDEHCERLPYDASKWEFPRDRLKLGKPLGRGAFGQVIE
ADAFGIDKTATCRTVAVKMLKEGATHSEHRALMSELKILIHIGHHLNVVN
LLGACTKPGGPLMVIVEFCKFGNLSTYLRSKRNEFVPYKTKGARFRQGKD
YVGAIPVDLKRRLDSITSSQSSASSGFVEEKSLSDVEEEEAPEDLYKDFL
TLEHLICYSFQVAKGMEFLASRKCIHRDLAARNILLSEKNVVKICDFGLA
RDIYKDPDYVRKGDARLPLKWMAPETIFDRVYTIQSDVWSFGVLLWEIFS
LGASPYPGVKIDEEFCRRLKEGTRMRAPDYTTPEMYQTMLDCWHGEPSQR
PTFSELVEHLGNLLQANAQQDGKDYIVLPISETLSMEEDSGLSLPTSPVS
CMEEEEVCDPKFHYDNTAGISQYLQNSKRKSRPVSVKTFEDIPLEEPEVK
VIPDDNQTDSGMVLASEELKTLEDRTKLSPSFGGMVPSKSRESVASEGSN
QTSGYQSGYHSDDTDTTVYSSEEAELLKLIEIGVQTGSTAQILQPDSGTT
LSSPPV

---

We claim:

1. A method of treating advanced or metastatic Epithelial Growth Factor Receptor (EGFR) T790M-positive non-small cell lung cancer in a human patient comprising administering to the patient an antibody comprising a heavy chain having a heavy chain variable region having the amino acid sequence of SEQ ID NO: 2 and a light chain having a light chain variable region having the amino acid sequence of SEQ ID NO: 1 at a dose of about 6 mg/kg to about 10 mg/kg on day 1 of a 14 day cycle, in combination with osimertinib or a pharmaceutically acceptable salt thereof administered orally at a daily dose of about 40 mg to about 80 mg.

2. The method of claim 1, wherein the heavy chain has the amino acid sequence of SEQ ID NO: 4 and the light chain has the amino acid sequence of SEQ ID NO: 3.

3. The method of claim 1, wherein the patient has received treatment with gefitinib, erlotinib, or afatinib prior to receiving the antibody.

4. The method of claim 1, wherein the cancer further comprises at least one additional EGFR activating mutation selected from the group consisting of a deletion of exon 19 and a L858R mutation in exon 21.

5. The method of claim 1, wherein the patient is administered 10 mg/kg of the antibody.

6. The method of claim 1, wherein the patient is administered 80 mg of osimertinib or a pharmaceutically acceptable salt thereof.

7. The method of claim 1, wherein the patient is administered a mesylate salt of osimertinib.

8. The method of claim 1, wherein the antibody is ramucirumab, and wherein the cancer further comprises at least one additional EGFR activating mutation selected from the group consisting of a deletion of exon 19 and an a L858R mutation in exon 21.

9. The method of claim 1, wherein the cancer has metastasized to the central nervous system.

10. The method of claim 8, wherein the cancer has metastasized to the central nervous system.

11. The method of claim 1, wherein the patient responds to treatment with stable disease, a partial response, or a complete response.

12. The method of claim 8, wherein the patient responds to treatment with stable disease, a partial response, or a complete response.

* * * * *